Figure 1:
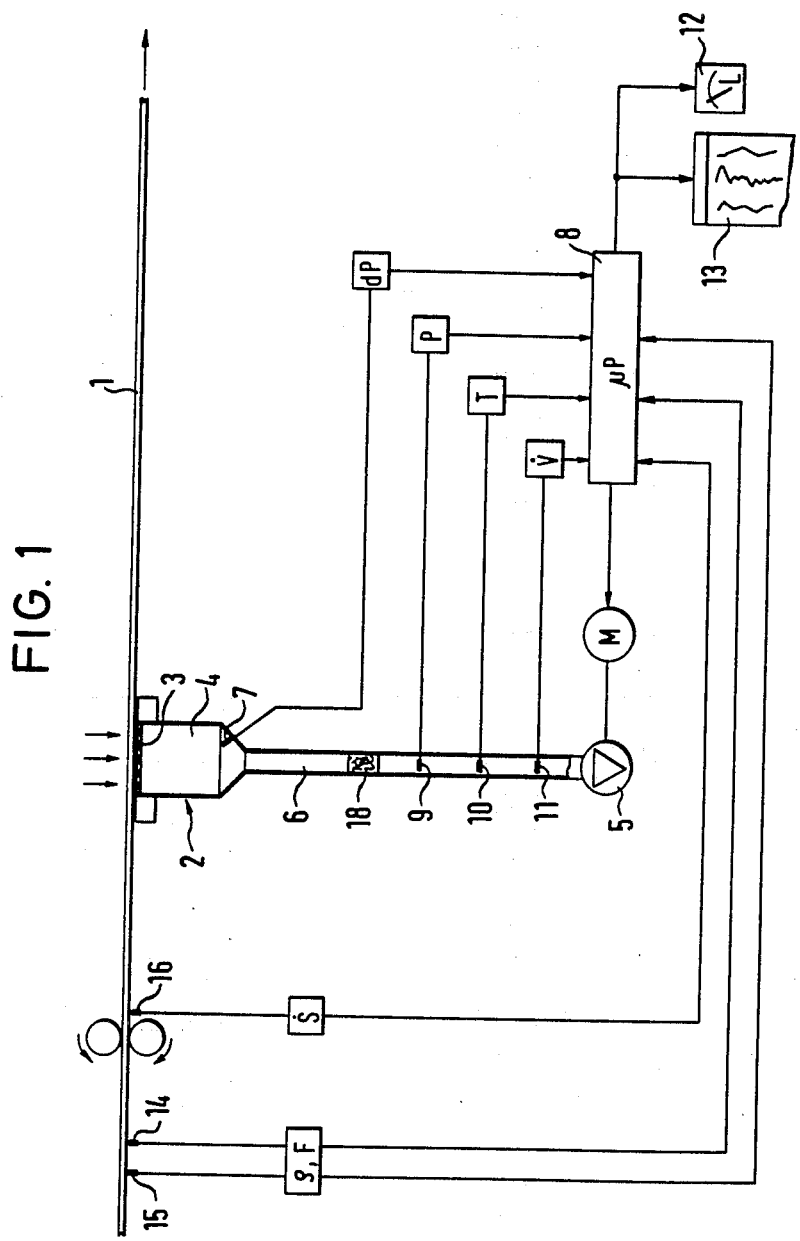

United States Patent [19]

Schuster et al.

[11] Patent Number: 4,676,091
[45] Date of Patent: Jun. 30, 1987

[54] METHOD AND DEVICE FOR CONTINUOUS MEASUREMENT OF POROSITY

[75] Inventors: Hans K. Schuster, Bruckmühl; Jens-Peter Heins, Feldkirchen-Westerham; Bernhard Gockel, Germering; Holger Schmidt, Munich, all of Fed. Rep. of Germany

[73] Assignee: Gessner & Co. GmbH, Mangfall, Fed. Rep. of Germany

[21] Appl. No.: 881,968

[22] Filed: Jul. 3, 1986

[30] Foreign Application Priority Data

Oct. 24, 1985 [DE] Fed. Rep. of Germany ....... 3537896

[51] Int. Cl.⁴ .............................................. G01N 15/08
[52] U.S. Cl. ......................................... 73/38; 73/37.7
[58] Field of Search .................................. 73/38, 37.7

[56] References Cited

U.S. PATENT DOCUMENTS 4,311,037 1/1982 Gotchel et al. ........................ 73/38

FOREIGN PATENT DOCUMENTS 2095411 9/1982 United Kingdom ..................... 73/38

Primary Examiner—Stewart J. Levy
Assistant Examiner—Joseph W. Roskos
Attorney, Agent, or Firm—Louis Orenbuch; George Greenfield

[57] ABSTRACT

The porosity of a strip of material is continuously computed by causing air to be drawn through the material as the strip moves across a perforated head situated atop a chamber in which the pressure is reduced by suction. In one embodiment, the reduced pressure is held substantially constant while the amount of air drawn through the chamber is measured and the porosity is determined by a computer whose inputs include the measured volume of air flow through the chamber and the speed at which the strip moves across the head, in addition to other inputs. In another embodiment, the volume of air flowing through the chamber is held substantially constant while the pressure in the chamber is measured and used as an input to the computer. In both embodiments, the speed at which the strip moves across the head is employed as a factor in the porosity computation.

20 Claims, 2 Drawing Figures

METHOD AND DEVICE FOR CONTINUOUS MEASUREMENT OF POROSITY

The invention relates to a method for continuous measurement of the porosity of a moving strip of porous material, in which the strip is moved over a measuring head, this strip forms a laterally sealed measuring chamber in combination with the measuring head, a low pressure is produced within this measuring chamber, this low pressure is continuously measured and controlled to a predetermined constant value, as a result of the low pressure air flows through the porous strip into the measuring chamber and is sucked therefrom, the amount of air flowing through the measuring chamber is measured, and from this measured value the porosity of the moving strip is continuously computed. Instead of controlling the low pressure created in the measuring chamber to a predetermined constant value and measuring the air flowing through the measuring chamber, alternatively also the amount of air flowing can be controlled to a predetermined constant value and the resulting low pressure in the measuring chamber can be continuously measured in order thereby to determine the porosity.

The invention relates furthermore to apparatus for carrying out the measuring method, comprising a measuring head across which the strip is moved, an air-tight measuring chamber formed from the combination of the moving strip and the measuring head, an arrangement for producing a low pressure within this measuring chamber, a measurement sensor for the measuring chamber for continuous measurement of the low pressure, a control arrangement connected to this measurement sensor for controlling the low pressure to a predetermined constant value, a measuring arrangement for measuring the amount of air flowing through the porous strip and the measuring chamber, and an electronic evaluating arrangement connected to this measuring arrangement for continuously computing the porosity of the moving strip from the measured amount of air. According to the alternative measuring method, instead of the measuring sensor for measuring the low pressure, also a measuring arrangement for continuously measuring the amount of air flowing through the porous strip and the measuring chamber can be provided, a corresponding control arrangement controlling the flowing amount of air to a predetermined constant value and instead of the measuring arrangement for measuring the air flowing through the porous strip and the measuring chamber, a measurement sensor is provided within the measuring chamber for continuous measurement of the low pressure present therein, so that then the continuously measured low pressure serves as a measure of the porosity.

The continuous measurement of the porosity of a moving strip is in particular of great significance in the manufacture of filter papers, fibre fleeces and other porous web materials, if during the continuous manufacturing process on-line quality control is required or predetermined manufacturing parameters, such as for example the degree of comminution or the mixture proportion of the raw material is to be continuously changed by process control in dependence upon the measured porosity. The strip whose porosity is to be measured moves with relatively high speed across the measuring station. Since the porous strip itself forms a part of the measuring chamber, in which either the existing low pressure or the amount of air flowing therethrough is to be maintained constant, lateral sealing between the upper edge of the measuring chamber and the strip sliding thereover must be ensured. This is achieved only to a certain extent, so that the measuring errors resulting from the surrounding air must be compensated by other measures.

From U.S. Pat. No. 4,311,037, apparatus of the type mentioned in the introduction for measuring porosity is known, in which the low pressure present in the measuring chamber or the volume flow of the air flowing through the porous strip and the measuring chamber is controlled to a predetermined constant value by means of a control arrangement which operates an electromotor driven low pressure blower. It has however been shown that such a simple control arrangement is unable to compensate the rapid variations of the low pressure present in the measuring chamber or of the amount of air flowing therethrough in such manner that the necessary boundary condition for sufficiently exact porosity measurement, that is to say maintaining constant either the low pressure or the amount of air flow, can be regarded as fulfilled. As a consequence, measuring errors occur to an extent which can no longer be tolerated with the high demands on exactitude of the porosity measurement. Moreover, in the known measuring device variations of quality parameters of the porous strip and the strip speed are not taken into account, which results in additional measuring errors.

It is therefore an object of the present invention to propose a method for continuous measurement of porosity of a moving strip and apparatus for carrying out the method, in which the described disadvantages do not occur and which display particularly improved measuring precision.

In the method according to the invention, the low pressure created in the measuring chamber or the amount of air flowing through the measuring chamber is maintained as nearly constant as possible by means of a control arrangement, the unavoidably occurring control errors are, however, accepted and are mathematically compensated in the determination of the porosity from the measured values. If, for example, the method operates with constant low pressure in the measuring chamber, and if the amount of air flowing through the measuring chamber serves as a basis for the determination of the porosity of the strip, then additionally the instantaneously occurring low pressure is measured, and its temporal variation is included as a correction function in the computation of the porosity. This has the great advantage that the control of the low pressure to a constant value nee only be sufficiently exact as is possible with economically acceptable expense, but however, the precision achieved is in spite of that substantially higher than is the case with conventional measuring methods without additional allowance for the temporal variation of the low pressure. With the method according to the invention, an exact porosity measurement is even possible if control errors up to about 50% are permitted.

Also in the apparatus according to the invention for carrying out the continuous porosity measurement, the substantial improvement of precision is achieved with relatively simple technical means; it requires only an additional measuring sensor to be provided for the measuring chamber for continuous measurement of the low pressure, which sensor is connected directly to the evaluating arrangement for computation of the porosity of the moving strip from the likewise measured amount of air, so that the temporal variation of the low pressure can be allowed for in the porosity determination. If the measuring device operates with constant amount of air instead of constant low pressure, an additional measuring device for continuous measurement of the amount of air flowing through the porous strip and the measuring chamber must be provided and be connected directly to the evaluating arrangement so that the temporal variation of the amount of air flow can be taken into account.

Expediently, the measurement of the amount of air flowing through the measuring chamber can be achieved by volume flow measurement or measurement of the mass flow. Then a volume flow arrangement or a mass flow arrangement is provided in the corresponding device. Such measuring arrangements as electrical anemometers or thermic mass flow meters are available.

The precision of the porosity measurement can be increased further if additional quality parameters of the strip are measured and are likewise taken into account in the computational determination of the porosity. Such quality parameters influencing the porosity are for example the mass per unit area, wetness, thickness and specific volume of the porous strip material. If these parameters are to be taken into account, additional measuring sensors are required on the measuring device which are connected to the evaluating arrangement.

Variations in the relative speed between the moving strip and the measuring head can likewise be a source of measuring errors. In a preferred embodiment of the invention, therefore also in addition the speed of the moving strip is determined by a speed measuring arrangement and is supplied to the evaluating arrangement in order that it can be taken into account in the form of a time-dependent correction factor in the computation of the porosity.

In a particularly advantageous embodiment of the measuring device according to the invention, a micro-computer is employed as an evaluating element. Such a commercially available micro-computer is able, during the computation of the porosity from the various measured quantities, to effect the necessary complex computations sufficiently quickly that the porosity is determined without any time lag, even with strips moving past the measuring head with high speed. The time shift between the change of porosity and the indication occurring in conventional methods as a result of the time-dependent regulation of the reduced pressure appearing in the measuring chamber or of the amount of air flowing therethrough, is prevented according to the present invention by the real-time determination of control errors and their immediate compensation in the computation of the porosity. This thus makes available for the first time a genuine on-line measuring signal for the strip porosity, which renders the method or device according to the invention particularly suitable for use within a process control in strip manufacture. The invention offers however equivalent advantages in the rapid detection of any holes which may be present in the strip material, in determination of localized distributional variations of the porosity (so-called "cloudiness" of the material) and in the recognition of contamination in or on the strip.

In a further advantageous embodiment of the invention, the control arrangement for maintaining a constnt reduced pressure in the measuring chamber or a constant amount of air flowing therethrough is integrated into the micro-computer representing the evaluating arrangement. By this means, the control precision is improved and the construction of the measuring device simultaneously simplified.

In order to prevent contamination of the sensitive measuring system a filter may be provided between the measuring chamber and the measuring arrangement for measuring the amount of air flow.

Figure 2:
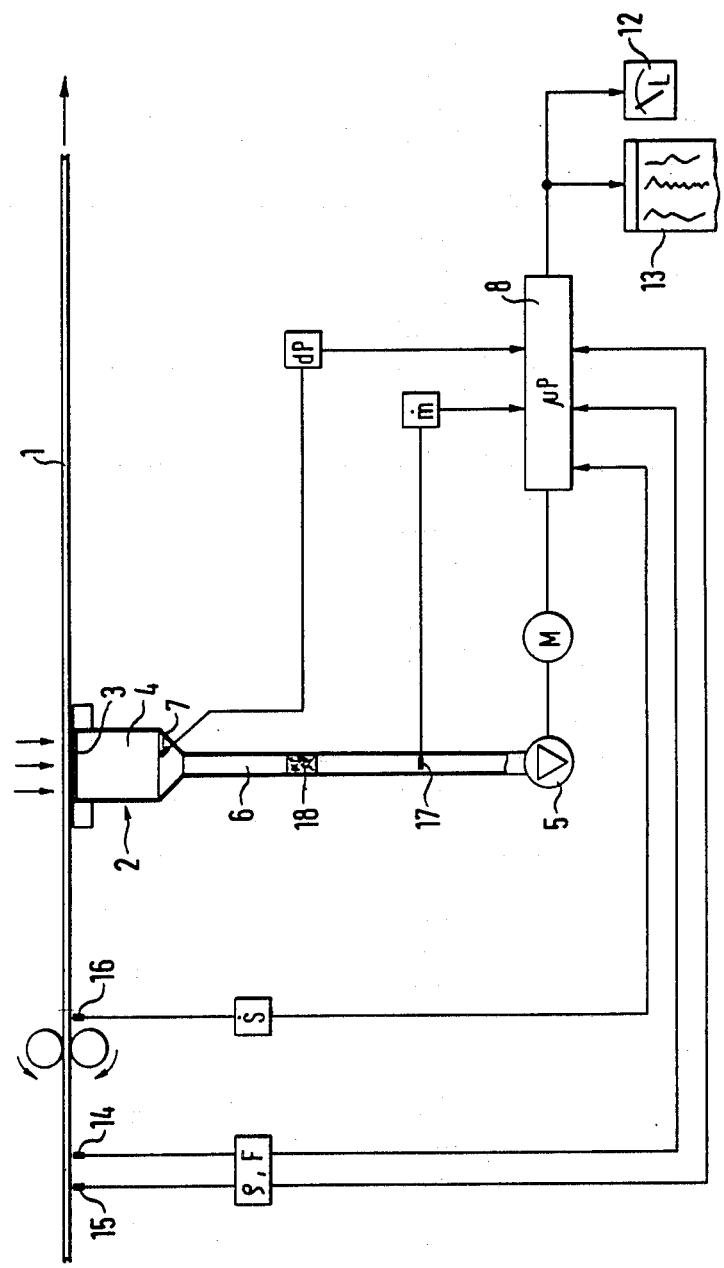

The method according to the invention and the device for carrying out the method will be described in the following by way of example with reference to the accompanying drawings, in which:

FIG. 1 shows a schematic diagram of a device for continuous measurement of the porosity according to the invention, the reduced pressure occurring in the measuring chamber of the measuring head being maintained constant and the volume flow and temperature and the absolute pressure of the air flowing through the measuring chamber being measured and the porosity being continuously determined therefrom; and FIG. 2 likewise shows a schematic diagram of in essence the device according to FIG. 1, in which however instead of the volume flow, the temperature and the absolute pressure of the mass flow of the air flowing through the measuring chamber are measured and the porosity is determined therefrom.

The porous strip 1 illustrated in FIG. 1 is moved over a measuring head 2. The upper surface of this measuring head 2 is formed from a measuring plate 3 in which a plurality of measuring openings are provided. The moving strip 1 is sucked onto the edge of the measuring plate 3 by means of a suction device which is not illustrated, so that the measuring head 2 in combination with the strip 1 forms a laterally sealed measuring chamber. An electromotor driven suction layer 5 produces a reduced pressure within the measuring chamber 4. As a result of this reduced pressure, air flows through the porous strip 1 into the measuring chamber 4 and is sucked away therefrom via a measuring chamber 6. The reduced pressure occurring in the measuring chamber 4 is continuously measured by a measuring sensor 7, which is connected to a micro-computer 8. Within the measuring channel 6 are provided further measuring sensors for determining the absolute pressure of the flowing air 9 and its temperature 10. The amount of air flowing through the measuring chamber 4 and the measuring channel 6 is measured by means of a volume flow measuring arrangement 11. The measuring sensors 8 and 9 and the volume flow measuring arrangement 11 are likewise connected to the micro-computer 8.

The measuring sensor 7 for the reduced pressure, the micro-computer 8 and the electromotor of the suction layer 5 controlled by the latter form a control circuit with the aid of which the reduced pressure occurring in the measuring chamber 4 is maintained as constant as possible. On the basis of the values measured by the measuring sensors 9 and 10 for the absolute pressure and temperature of the air guided through the measuring channel 6 as well as the measuring signal proportional to the volume flow delivered by the measuring arrangement 11, the micro-computer 8 computes continuously the porosity of the strip1 sliding across the measuring head 2. The porosity measured in this manner is displayed on a display device 12. For monitoring the localised variations of porosity along the strip 1, the continuously measured porosity value is moreover displayed by a chart recorder 13.

The micro-computer 8 uses the measuring signal delivered by the measuring sensor 7 for the reduced pressure occurring in the measuring chamber 4, not only for controlling the same to a predetermined constant value, but also to compensate the control error unavoidably occurring in spite of the control by additionally taking account of the temporal variation of the reduced pressure in the computation of the porosity. The micro-computer 8 thus fulfils a double function: it is both an evaluating arrangement for determining the porosity and also a control arrangement for maintaining constant the reduced pressure appearing in the measuring chamber 4.

Additional measuring sensors 14 and 15 are provided for measuring the wetness and the specific volume of the moving strip 1, which sensors are likewise electrically connected to the micro-computer 8. A speed sensor 16 is additionally connected for determining the instantaneous speed of the strip 1 moving across the measuring head 2. These additional measuring values are likewise included by the micro-computer 8 in the form of corresponding correction factors in the computation of the porosity. In order to protect the sensitive measuring system, a filter 18 is provided in the measuring channel 6.

In the arrangement illustrated in FIG. 2 for measuring the porosity of a moving strip 1, instead of the measuring sensors 9 and 10 for measuring the absolute pressure or the temperature and the volume flow measuring arrangement 11, a thermal mass flow meter 17 is employed, with which the amount of air sucked through the porous strip 1 and flowing through the measuring chamber 4 is measured. In this way, in turn the reduced pressure occurring in the measuring chamber 4 is maintained as constant as possible. Measured mass flow of the flowing air serves as a measure of the porosity, which is computed by the micro-computer 8, the pressure variations remaining in spite of the control being compensated by means of a correction factor which is a time function of the measured reduced pressure.

What is claimed is:

1. A method for continuously measuring the porosity of a moving strip of porous material, comprising the steps of
   (a) causing the strip to move over a measuring head which permits air to flow through the strip and into a measuring chamber;
   (b) causing a low pressure to be produced within the measuring chamber;
   (c) continuously measuring the low pressure in the chamber;
   (d) causing the low pressure in the chamber to be maintained at a substantially constant value;
   (e) measuring the amount of air flow through the measuring chamber;
   (f) measuring the speed at which the strip moves over the measuring head; and
   (g) causing the porosity of the moving strip to be continuously computed from the aforesaid measurements.

2. Method according to claim 1 wherein the measurement of the amount of air flowing through the measuring chamber is achieved by volume flow measurement.

3. Method according to claim 1 wherein the measurement of the amount of air flowing through the measuring chamber is achieved by mass flow measurement.

4. A method for continuously measuring the porosity of a moving strip of porous material, comprising the steps of
   (a) causing the strip to move over a measuring head which permits air to flow through the strip and into a measuring chamber;
   (b) causing a low pressure to be produced within the measuring chamber;
   (c) measuring the air flow through the measuring chamber;
   (d) causing the volume of air flow through the measuring chamber to be maintained substantially constant;
   (e) measuring the low pressure in the measuring chamber;
   (f) measuring the speed at which the strip moves over the measuring head; and
   (g) causing the porosity of the moving strip to be continuously computed from the aforesaid measurements.

5. Method according to claim 4 wherein the measurement of the amount of air flowing through the measuring chamber is achieved by volume flow measurement.

6. Method according to claim 4 wherein the measurement of the amount of air flowing through the measuring chamber is achieved by mass flow measurement.

7. In apparatus for continuously measuring the porosity of a moving strip of porous material where the apparatus is of the kind having
   (a) a measuring head across which the strip is moved,
   (b) means cooperating with the measuring head and the moving strip for providing a measuring chamber,
   (c) means for lowering the pressure in the measuring chamber,
   (d) pressure measurement means for providing a continuous mesurement of the pressure in the measuring chamber as the moving strip crosses the measuring head,
   (e) control means responsive to the pressure measurement means for maintaining a substantially constant low pressure in the measuring chamber,
   (f) air flow measurement means for continuously measuring the amount of air flow through the measuring chamber, and
   (g) computer means responsive to the air measurement means for continuously computing the porosity of the moving strip, said computer means being responsive to the pressure measurement means for including temporal variations in the substantially constant low pressure in the measuring chamber in the porosity computation;
the improvement comprising speed sensing mens for continuously detecting the speed at which the moving strip crosses the measuring head and providing to the computer means an input related to that speed for use by the computer means as a factor in the measurement of the porosity of the strip.

8. Apparatus according to claim 7 wherein the air flow measurement means is a volume flow measuring apparatus.

9. Apparatus according to claim 8 wherein the air flow measurement means is an electrical anemometer.

10. Apparatus according to claim 7 wherein the air flow measurement means is a mass flow measuring apparatus.

11. Apparatus according to claim 10 wherein the air flow measurement means is a thermic mass flow measuring device.

12. Apparatus according to claim 7 wherein said computer means further comprises the control arrangement for the constant low pressure.

13. Apparatus according to claim 7 wherein a filter is provided between the measuring chamber and the measuring arrangement for measuring the amount of air flow.

14. In apparatus for continuously measuring the porosity of a moving strip of porous material where the apparatus is of the kind having
   (a) a measuring head across which the strip is moved,
   (b) means cooperating with the measuring head and the moving strip for providing a measuring chamber,
   (c) means for lowering the pressure in the measuring chamber,
   (d) pressure measurement means for providing a continuous measurement of the pressure in the measuring chamber as the moving strip crosses the measuring head,
   (e) air flow measurement means for continuously measuring the amount of air flow through the measuring chamber;
   (f) control means connected to the air flow measurement means for maintaining a substantially constant volume of air flow through the measuring chamber; and
   (g) computer means responsive to the air measurement means for continuously computing the porosity of the moving strip; said computer means being responsive to the pressure measurement means for including temporal variations in the amount of air flowing through the measuring chamber in the computation of the porosity;

the improvement comprising speed sensing means for continuously detecting the speed at which the moving strip crosses the measuring head and providing to the computer means an input related to that speed for use by the computer means as a factor in the measurement of the porosity of the strip.

15. Apparatus according to claim 14 wherein the air flow measurement means is a volume flow measuring apparatus.

16. Apparatus according to claim 15 wherein the air flow measurement means is an electrical anemonmeter.

17. Apparatus according to claim 14 wherein the air flow measurement means is a mass flow measuring apparatus.

18. Apparatus according to claim 17 wherein the air flow measurement means is a thermic mass flow measuring apparatus.

19. Apparatus according to claim 14 wherein the computer means causes the control means to maintain a substantially constant volume of airflow through the measuring chamber.

20. Apparatus according to claim 14 further including air filtration means disposed between the measuring chamber and the air flow measurement means.

* * * * *